United States Patent [19]

Boschi et al.

[11] 4,236,017
[45] Nov. 25, 1980

[54] PROCESS FOR SYNTHESIZING 2-SUBSTITUTED SEMICARBAZONES AND CARBALKOXY HYDRAZONES

[75] Inventors: Pier M. Boschi, Piacenza; Franco Gozzo, San Donato, both of Italy

[73] Assignee: Montedison S.p.A., Milan, Italy

[21] Appl. No.: 61,241

[22] Filed: Jul. 27, 1979

[51] Int. Cl.³ .................. C07C 125/06; C07C 133/04; C07C 133/08
[52] U.S. Cl. ...................................... 560/24; 560/27; 560/159; 564/36
[58] Field of Search .................. 260/552 SC, 554; 560/24, 27, 159

[56] References Cited

U.S. PATENT DOCUMENTS 3,304,327  2/1967  Rapaelian et al. .................. 260/554

FOREIGN PATENT DOCUMENTS 50-25455  8/1975  Japan .................................... 260/554

OTHER PUBLICATIONS

"Chemistry of Carbon Compounds", Ed. E. H. Rodd, vol. IB, pp. 918–919 (1952).
"Organic Synthesis", Collective vol. II, pp. 395 (1950).

*Primary Examiner*—Thomas A. Waltz

[57] ABSTRACT

Semicarbazones and carbalkoxy hydrazones substituted in 2 position are synthesized by alkylation of the corresponding semicarbazones and carbalkoxy hydrazones, using alkyl halides or alkyl sulphates as alkylating agents.

10 Claims, No Drawings

PROCESS FOR SYNTHESIZING 2-SUBSTITUTED SEMICARBAZONES AND CARBALKOXY HYDRAZONES

THE PRIOR ART

The synthesis of 2-alkyl-semicarbazones (I) in general can be achieved by additioning an alkyl-hydrazine (II) to an alkaline cyanate in an aqueous medium, thereby obtaining a semicarbazide (III) which, in its turn, is reacted with an aldehyde or a ketone according to the following reactions scheme:

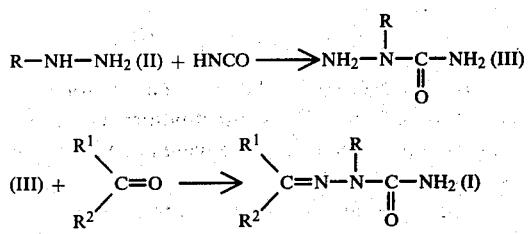

(Scheme 1).

[See, for instance, "Chemistry of Carbon Compounds", Ed. E. H. Rodd, Vol. IB, pages 918–919 (1952).]

That process, which is well known in organic chemistry, has the disadvantage of requiring, as starting material, alkyl-hydrazines that are very expensive compounds difficult to prepare, particularly when the alkyl group is a primary one.

The main methods for the preparation of alkylhydrazines consist in reacting:

(1) an alkyl-urea with hypochlorite and then with sodium hydroxide, U.S. Pat. No. 2,917,545, 1957, which method, however, has the drawbacks of operating in diluted solutions and giving rather low yields;

(2) methyl sulphate with an azine obtained by the reaction of hydrazine with benzaldehyde and by then hydrolizing the quaternary salt obtained:

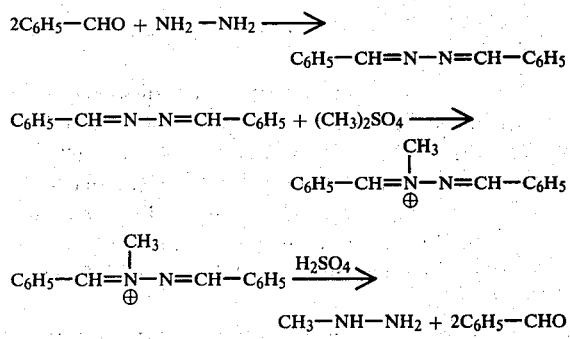

[See Organic Synthesis, Collective Vol. II, 395 (1950)]

This method, besides being rather complicated, has the disadvantage of being limited to the preparation of methylhydrazine; in fact, different alkylating agents do not quaternize with the azine.

Furthermore, the direct alkylation of hydrazine is not suitable for obtaining mono-alkyl-hydrazine with acceptable yields.

The preparation of the 2-alkyl-semicarbazones may be achieved by preparing, independently from the alkyl-hydrazine, the 2-alkyl-semicarbazide (Compound III, scheme 1). However, the method of preparation usually used involves the catalytic reduction of alkyl-nitrous-urea of the formula:

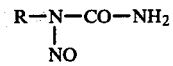

See U.S. Pat. No. 3,387,030. Such process presents two serious drawbacks represented by the necessity of using compounds that carry the group

which has been recognized as being carcinogenic, and by the impossibility of obtaining high yields.

The preparation of 2-alkyl-carbalkoxy-hydrazones (V) is usually achieved by reacting an aldehyde or ketone with a 2-alkyl-2-carbalkoxy-hydrazine (IV)

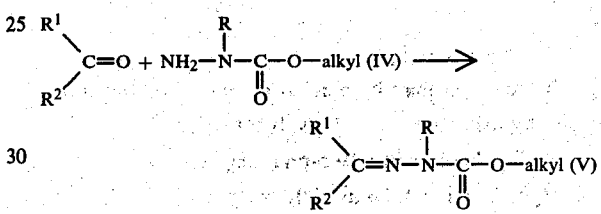

The 2-alkyl-2-carbalkoxy-hydrazines (IV) however, are prepared starting from alkyl-hydrazines (II) with the drawbacks mentioned hereinabove.

THE PRESENT INVENTION

An object of the present invention is to provide a general method for the preparation of 2-alkyl-semicarbazones and 2-alkyl-carbalkoxy-hydrazones which does not involve the drawbacks and disadvantages of the prior art processes.

This and other objects are achieved by this invention in accordance with which 2-alkyl-semicarbazones and 2-alkyl-carbalkoxy-hydrazones are prepared by alkylating with alkyl halides or with alkyl sulphates the corresponding semicarbazones or carbalkoxy-hydrazones.

This method is surprisingly endowed with a high selectivity. In fact, the alkylation is exclusively oriented towards position 2 and no alkylation products in position 1 or 4 can be observed. This great selectivity is even more surprisingly maintained also when olefinic substituents are present in the semicarbazone molecule and which could be attacked by the alkylating agent.

The present synthesis method has proved to be of general validity inasmuch as the alkylation reaction may be carried out on semicarbazones or carbalkoxy-hydrazones of various carbonyl derivatives, by using as alkylating agents alkyl, benzyl, allyl or propargyl halides.

The selectivity and general validity of the method are maintained also when the alkylation of carbalkoxy-hydrazones is carried out according to the following schematic reaction:

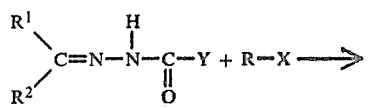

(VI)

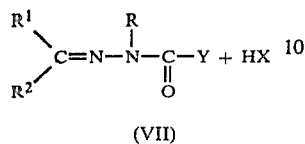

(VII)

wherein:

R=alkyl, allyl, propargyl or benzyl, which can also be substituted;

X=Cl, Br, I, or SO$_4$R in which R has the same meaning as stated above;

R$^1$ and R$^2$ (equal to or different from each other)=H or alkyl, aryl or vinyl radicals which can be substituted; and Y=NH$_2$ or O-alkyl.

The reaction may be carried out in a homogeneous phase by using aprotic polar solvents in the presence of an alkaline base or in a two-phase system consisting of an organic solvent immiscible with water and of an aqueous solution of an alkaline base, in the presence of a phase-transfer catalyst such as a quaternary ammonium salt.

The duration of the reaction amounts to about 3–4 hours and a slight heating (50°–60° C.) facilitates its course.

The 2-alkyl-semicarbazones are intermediates that are useful in the synthesis of pesticides. In fact, by cyclization there are obtained 1,2,4-triazol-5-ones from which it is possible to obtain phosphoric esters endowed with an insecticide, nematocide and acaricide activity, as described in Italian Applications Nos. 29,420 A/76 and 20,855 A/77.

2-alkyl-carbalkoxy-hydrazones are useful intermediates for the preparation of alkyl-hydrazines (by hydrolysis) or of 2-alkyl-semicarbazones (by treatment with NH$_3$).

The following examples are given to illustrate the invention in more detail and are not intended to be limiting. Some of the examples illustrate alkylation reactions conducted on a semicarbazone of a particular nature, that is, β,β-dichloroacrylidene-semicarbazone (obtained by condensation between β,β-dichloroacrolein and semicarbazide) which show how the selectivity of the reaction is maintained also when unsaturated olefinic-type groups are present in the semicarbazone molecule.

EXAMPLE 1

Preparation of β,β-dichloroacrylidene-2-ethyl-semicarbazone in a Homogeneous Phase

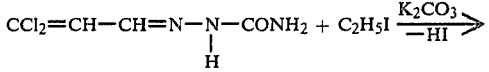

(1)

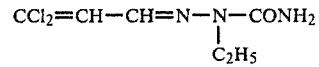

(2)

1.82 g of β,β-dichloroacrylidene-semicarbazone (1) were dissolved in 30 ml of N,N-dimethylformamide and to the solution thus obtained there were added 2.3 g of K$_2$CO$_3$ and 1.93 g of C$_2$H$_5$I.

The reaction mixture was subjected to stirring for 3 hours at 50°–60° C., then cooled down to 20° C., additioned with 120 ml of H$_2$O and extracted with ethylacetate (2×100 ml). The organic solution was anhydrified with anhydrous Na$_2$SO$_4$, and the solvent was thereafter evaporated. Thereby were obtained 1.1 g of a yellowish solid consisting of β,β-dichloroacrylidene-2-ethyl-semicarbazone (2) which crystallizes from ethyl ether: m.p.=127°–128° C. (compound No. 3, Table I).

EXAMPLE 2

Preparation of β,β-dichloroacrylidene-2-methyl-semicarbazone

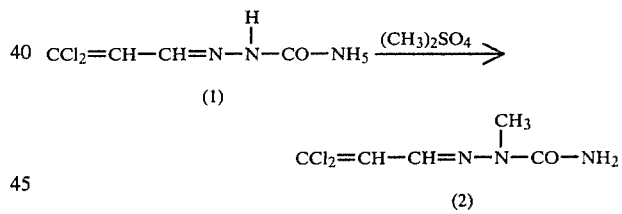

(1)

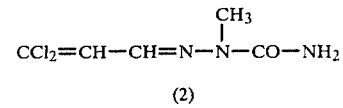

(2)

In 20 ml of methylene chloride were dissolved 1.8 g of β,β-dichloroacrylidene-semicarbazone, 1.5 ml of (CH$_3$)$_2$SO$_4$ and 0.1 g of trimethyl-cetylammonium-bromide. An aqueous solution of NaOH (50% concentration, 3 ml) was added to the solution. This heterogeneous reaction mixture was thereupon vigorously stirred for 3–4 hours and then additioned with 20 ml of water.

The organic phase was separated, anhydrified with anhydrous Na$_2$SO$_4$ and filtered, whereupon the solvent was evaporated thereby obtaining 1.7 g of a white solid consisting of β,β-dichloroacrylidene-2-methyl-semicarbazone (2) which crystallized from benzene: m.p.=130°/2° C. (compound No. 1, Table I).

EXAMPLE 3

Operating according to Examples 1 and 2, the β,β-dichloro-2-alkyl-semicarbazones shown in Table I were also prepared.

TABLE I

Compounds of the formula: $CCl_2=CH-CH=N-\underset{\underset{R}{|}}{N}-CO-Y$

| Compound No. | R | Y | m.p. (°C.) | Elementary Analysis (%) Theoretical C | N | Found C | N | Yield on converted product (%) |
|---|---|---|---|---|---|---|---|---|
| 1 | $CH_3$ | $NH_2$ | 130°–132° | 30.63 | 21.43 | 31.20 | 22.10 | 95 |
| 2 | $CH_3$ | $OC_2H_5$ | 77°–78° | 37.35 | 12.45 | 38.28 | 12.71 | 90 |
| 3 | $C_2H_5$ | $NH_2$ | 127°–128° | 34.20 | 20.0 | 34.90 | 20.12 | 95 |
| 4 | $CH_2-CH=CH_2$ | $NH_2$ | 107°–108° | 37.86 | 18.92 | 38.17 | 18.70 | 80 |
| 5 | $CH_2-C\equiv CH$ | $NH_2$ | | 38.20 | 19.09 | 38.12 | 18.79 | 80 |
| 6 | $CH_2-C_6H_5$ | $NH_2$ | 128°–130° | 48.55 | 15.44 | 49.65 | 15.70 | 60 |

EXAMPLE 4

The following example demonstrates the high selectivity of the process of this invention.

Preparation of
β,β-dichloroacrylidene-2-ethyl-semicarbazone

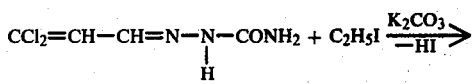

(1)

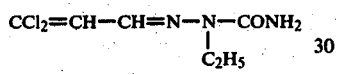

(2)

To a solution of 1.82 g of β,β-dichloroacrylidene-semicarbazone (1) in 30 ml of N,N-dimethylformamide, there were added 2.3 g of $K_2CO_3$ and 1.93 g of $C_2H_5I$.

The reaction mixture was stirred 3 hours at 50°–60° C., then cooled to 20° C. and additioned with 120 ml of $H_2O$. A solid product separated which was collected by filtration, washed with water and dried. Thereby, 2 g of a yellowish solid were obtained which was then suspended in ethyl acetate (100 ml).

The insoluble product was collected by filtration and washed with ethylacetate (30 ml). Thereby were recovered 0.8 g of unreacted β,β-dichloroacrylidene-semicarbazone. The ethyl acetate solutions were gathered together and the solvent was evaporated, obtaining 1.1 g of β,β-dichloroacrylidene-2-ethyl-semicarbazone (yellow solid, m.p. 127°–128° C.). Conversion: 55%, yield on converted product: 95%.

EXAMPLE 5

Preparation of benziliden-2-methyl-semicarbazone (2)

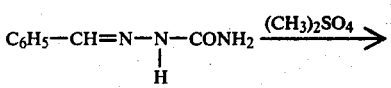

(1)

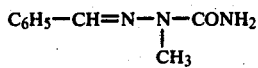

(2)

In 20 ml of methylene chloride there were dissolved 1.63 g of benziliden-semicarbazone (1), 1.5 ml of $(CH_3)_2SO_4$ and 0.1 g of trimethyl-cetylammonium bromide. To this solution, there was added an aqueous solution of NaOH (50% concentration, 3 ml) and the resulting heterogeneous mixture was stirred for 3 hours.

20 ml of water were then added to the mixture and the organic phase was separated and anhydrified on anhydrous $Na_2SO_4$ and filtered. The solvent was evaporated, thereby obtaining 1.7 g of (2) (m.p. 160° C.); yield on converted product 97%.

What is claimed is:

1. Process for the preparation of compounds of general formula:

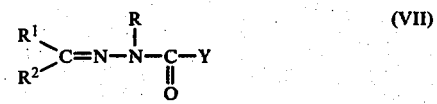

wherein R is alkyl, allyl, propargyl or benzyl radical or a substituted alkyl, allyl, propargyl or benzyl radical; $R^1$ and $R^2$, equal to or different from each other are H, or alkyl, aryl or vinyl radicals or substituted alkyl, aryl or vinyl radicals; and Y is $NH_2$ or O-alkyl, said process comprising reacting a compound of general formula:

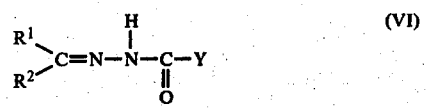

wherein $R^1$, $R^2$ and Y have the same meanings as in formula VII, with a halide or a sulphate of the formula: R-X in which X is Cl, Br, I or $SO_4R$ and R has the same meaning as in formula VII.

2. The process of claim 1, in which the reaction between the compound of general formula (VI) and the alkyl halide or alkyl sulphate is conducted in the presence of an alkaline base and in an aprotic polar solvent.

3. The process of claim 2 in which the aprotic polar solvent is dimethylformamide.

4. The process of claim 2, in which the alkaline base is potassium carbonate.

5. The process of claim 1, in which the reaction between the compound of general formula (VI) and the alkyl halide or alkyl sulphate is carried out at 50°–60° C. for a period of 3 to 4 hours.

6. The process of claim 1, in which the reaction between the compound of general formula (VI) and the alkyl halide or alkyl sulphate is carried out in a two-phase system consisting of an organic solvent immiscible with water and of an aqueous solution of an alkaline base, in the presence of a phase transfer catalyst.

7. The process of claim 6, in which the organic solvent is methylene chloride.

8. The process of claim 6, in which the aqueous solution of the alkaline base is an aqueous NaOH solution at about 50% concentration.

9. The process of claim 6, in which the phase transfer catalyst is a quaternary ammonium salt.

10. The process of claim 1, in which the reaction mixture is subjected to a vigorous stirring for from 3 to 4 hours.

* * * * *